United States Patent [19]

Rossetti et al.

[11] 4,217,277
[45] Aug. 12, 1980

[54] PROCESS FOR PRODUCING 3-AMINO-RIFAMYCINS S AND SV

[75] Inventors: Vittorio Rossetti; Leonardo Marsili; Carmine Pasqualucci, all of Milan, Italy

[73] Assignee: Archifar Laboratori Chimico Farmacologici S.p.A., Milan, Italy

[21] Appl. No.: 16,006

[22] Filed: Feb. 28, 1979

[30] Foreign Application Priority Data

Mar. 9, 1978 [GB] United Kingdom ............... 929578

[51] Int. Cl.$^2$ .......................................... C07D 413/04
[52] U.S. Cl. ............................................ 260/239.3 P
[58] Field of Search ................................ 260/239.3 P

[56] References Cited

U.S. PATENT DOCUMENTS 3,342,810  9/1967  Maggi et al. ................ 260/239.3 P

FOREIGN PATENT DOCUMENTS 1670479  1/1971  Fed. Rep. of Germany .... 260/239.3 P
1670377  2/1974  Fed. Rep. of Germany .... 260/239.3 P
2548128  5/1976  Fed. Rep. of Germany .... 260/239.3 P

OTHER PUBLICATIONS

March "Advanced Organic Chemistry", pp. 341, 897–898, 488–494, (McGraw–Hill) (1968).
Morrison and Boyd, "Organic Chemistry", (3rd Ed.) pp. 826–832 (Allyn and Bacon) (1973).
Kump et al., "Helvetica Chimica Acta", vol. 56, p. 2368 (1973).

Primary Examiner—John M. Ford
Assistant Examiner—Robert T. Bond
Attorney, Agent, or Firm—Oblon, Fisher, Spivak, McClelland & Maier

[57] ABSTRACT

Method of preparing 3-amino-rifamycins S and SV having antibiotic activity. According to such a method a 3-bromo-rifamycin S is reacted with sodium nitrite to give 3-nitro-rifamycin S which is reduced with zinc powder to give the 3-amino-rifamycin SV from which the 3-amino-rifamycin S can be obtained by treatment with an oxidating agent.

1 Claim, No Drawings

PROCESS FOR PRODUCING 3-AMINO-RIFAMYCINS S AND SV

The present invention relates to a process for the production of 3-amino-rifamycins S and SV.

3-amino-rifamycins S and SV are well known compounds provided with high antibiotic activities and are described in the German Pat. No. 1670377, in the German patent application DOS No. 1670479 and in Helvetica Chimica Acta, 56, 2368 (1973): they are obtained by reaction of rifamycin S with ammonia, but the yields are very low, less than 1%. It has also been found than the 3-amino-rifamycins S and SV are starting materials for the production of valuable rifamycin-derivatives provided with very high antibiotic properties, as disclosed in the U.S. Pat. No. 4,017,481 and in the Belgian Pat. Nos. 842036, 842.883, 848.185 and 848.186.

The U.S. Pat. No. 4,007,169 discloses a method according to which it is possible to produce 3-amino-rifamycins S and SV with high industrial yields: however such a method has the drawback of requiring the use of sodium azide as reactant which, as it is well known, is a highly toxic substance and may cause formation of detonating salts by reaction with metals like copper, iron, lead and so on.

According to the present invention it has now been found that 3-amino-rifamycins S and SV can be produced with yields higher than those achieved with the above mentioned art by reacting a 3-bromo-rifamycin S of formula

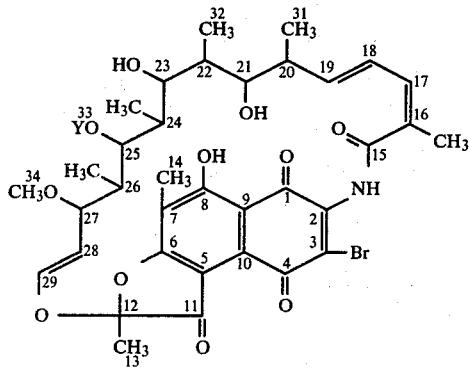

(I)

wherein Y is —H or —COCH₃, with sodium nitrite in N,N-dimethyl-formamide to give 3-nitro-rifamycins S of formula

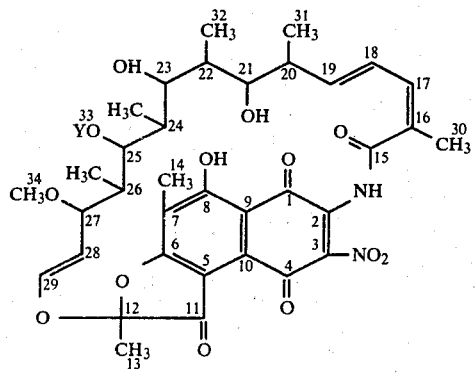

(II)

wherein Y is as above defined, and finally reducing the nitro group with a reducing agent consisting of zinc powder to give the 3-amino-rifamycin SV of formula

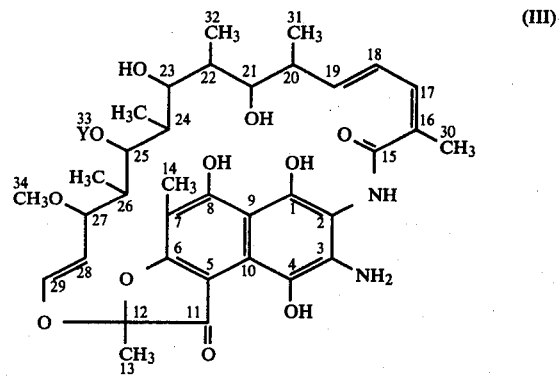

(III)

which by transformation in situ of the hydroquinon to quinon form by means of an oxidating agent selected from the group consisting of manganese dioxide, aqueous potassium ferricianide and aqueous magnesium persulfate, gives the 3-amino-rifamycin S of formula

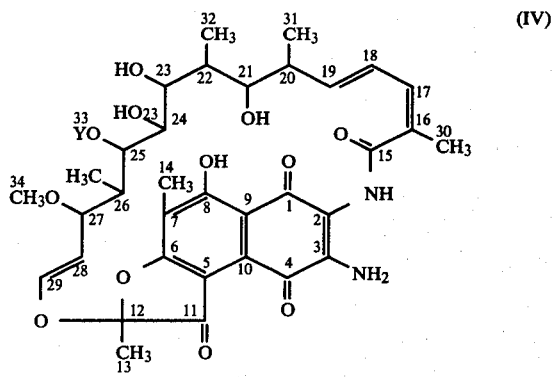

(IV)

The pathway of the reaction is represented by the following scheme:

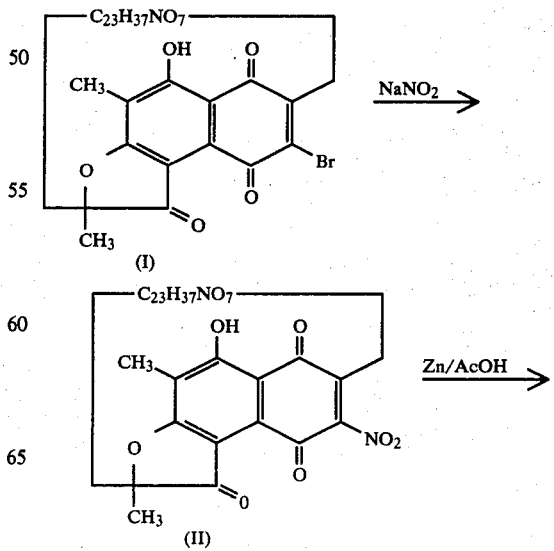

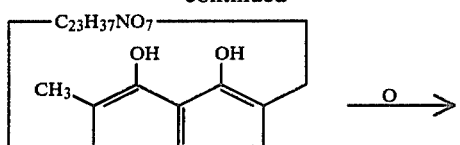

(III)

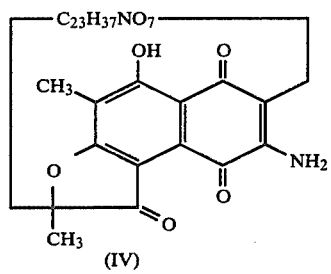

(IV)

The starting compound 3-bromo-rifamycin S of formula (I) is per se well known and is described in the German patent application DOS No. 2548128. In order that the characteristic features of the present invention be more clearly understood, the process will now be described by mere way of unrestrictive example.

EXAMPLE 1

540 g of 3-bromo-rifamycin S are dissolved in 1500 ml of N,N-dimethyl formamide at 20° C. A steam of $N_2$ is bubbled through the solution for 20', then 60 g of sodium nitrite are added portionwise allowing the temperature to rise to 39° C. while stirring under nitrogen atmosphere. The temperature is kept at 40° C. with a water bath for 30', then cooled at 20° C.; 10 g of urea are added and 70 ml of acetic acid are added dropwise. The steam of $N_2$ is stopped and 130 g of zinc powder are added portionwise with vigorous stirring and cooling with an ice bath to keep the temperature below 60° C. The reaction mixture is stirred allowing the temperature to decrease to room temperature, and stirring is continued for 5 hours. The reaction mixture is filtered and the solution is diluted with 3000 ml of dichloromethane and washed with water several times. The dichloromethane solution is treated with manganese dioxide in order to oxidize 3-amino-rifamycin SV to 3-amino-rifamycin S. After filtration and evaporation to dryness, raw material such obtained is crystallized from 600 ml of 2-methoxy-ethanol to give 440 g of TLC pure 3-amino-rifamycin S in black crystals. U.V.; I.R. and PMR are identical to an authenic sample prepared according to W. Kump, H. Bickel, Helv. Chem. Acta, 56(7), 2348 (1973).

EXAMPLE 2

10 g of 3-nitro-rifamycin S are suspended in 60 ml of dichloromethane, 5 ml of acetic acid are added and, while stirring, 1,7 g of zinc powder are added portionwise at such a rate to maintain the reaction mixture at gentle reflux; at the end of the addition the reaction mixture is warmed at gentle reflux for one hour, then cooled and filtered. The dichloromethane solution is treated with manganese dioxide in order to oxidize 3-amino-rifamycin SV to 3-amino-rifamycin S, filtered, evaporated to dryness and the black residue such obtained is crystallized by 2-methoxy-ethanol to give 8,65 g of pure 3-amino-rifamycin S.

What we claim is:

1. A process for producing 3-amino-rifamycins S and SV which comprises reacting a 3-bromo-rifamycin S of formula:

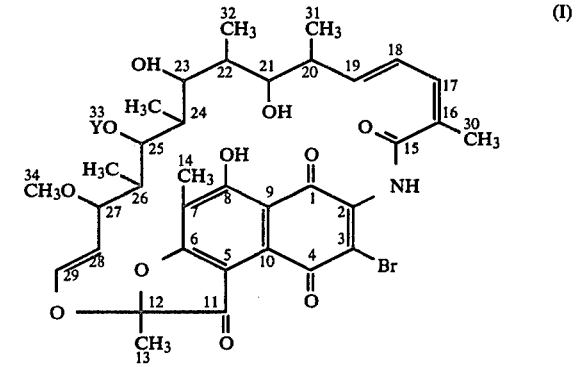

wherein Y is —H or —COCH₃ with sodium nitrite in N,N-dimethyl-formamide to give 3-nitro-rifamycins S of formula

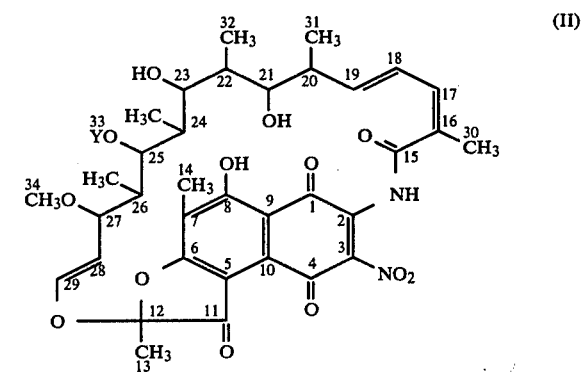

wherein Y is as above defined, and finally reducing the nitro group with a reducing agent consisting of zinc powder to give the 3-amino-rifamycin SV of formula:

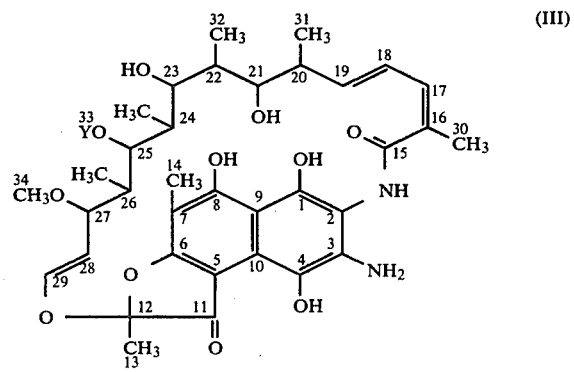

which by transformation is situ of the hydroquinon to quinon form by means of an oxidating agent selected from the group consisting of manganese dioxide, aqueous potassium ferricyanide and aqueous magnesium persulfate, gives the 3-amino-rifamycin S of formula
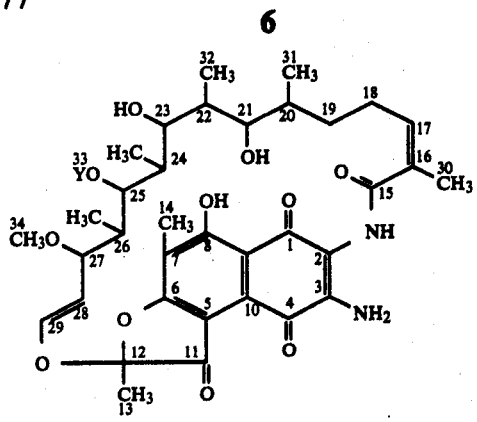
(IV)
* * * * *